United States Patent
Miles

(10) Patent No.: US 7,406,391 B2
(45) Date of Patent: Jul. 29, 2008

(54) SYSTEM, METHOD, AND COMPUTER PRODUCT FOR DETECTION INSTRUMENT CALIBRATION

(75) Inventor: Christopher Miles, Acton, MA (US)

(73) Assignee: Affymetrix, Inc., Santa Clara, CA (US)

( * ) Notice: Subject to any disclaimer, the term of this patent is extended or adjusted under 35 U.S.C. 154(b) by 221 days.

(21) Appl. No.: 11/231,266

(22) Filed: Sep. 20, 2005

(65) Prior Publication Data

US 2007/0239380 A1 Oct. 11, 2007

Related U.S. Application Data

(60) Provisional application No. 60/611,546, filed on Sep. 20, 2004.

(51) Int. Cl.
*G06F 19/00* (2006.01)
*G01B 11/14* (2006.01)

(52) U.S. Cl. .......................... 702/94; 356/622

(58) Field of Classification Search .......... 702/94, 702/95, 97, 85, 86, 127, 150; 356/614–616, 356/622, 318, 624; 250/252.1; 435/6; 382/128
See application file for complete search history.

(56) References Cited

U.S. PATENT DOCUMENTS

| | | | | |
|---|---|---|---|---|
| 6,066,448 | A * | 5/2000 | Wohlstadter et al. | 435/6 |
| 6,090,545 | A * | 7/2000 | Wohlstadter et al. | 435/6 |
| 6,143,152 | A | 11/2000 | Simpson et al. | |
| 6,185,030 | B1 * | 2/2001 | Overbeck | 359/225 |
| 6,191,802 | B1 | 2/2001 | Kessler | |
| 6,201,639 | B1 * | 3/2001 | Overbeck | 359/368 |
| 6,218,803 | B1 | 4/2001 | Montagu | |
| 6,225,625 | B1 * | 5/2001 | Pirrung et al. | 250/302 |
| 6,514,768 | B1 * | 2/2003 | Guire et al. | 436/518 |
| 6,531,864 | B2 | 3/2003 | Montagu | |
| 6,583,424 | B2 * | 6/2003 | Staton et al. | 250/461.2 |
| 6,687,395 | B1 | 2/2004 | Dietz et al. | |
| 6,740,871 | B1 * | 5/2004 | Staton et al. | 250/252.1 |
| 6,788,414 | B1 * | 9/2004 | Yeung et al. | 356/436 |
| 6,813,567 | B2 * | 11/2004 | Weiner et al. | 506/12 |
| 7,033,754 | B2 * | 4/2006 | Chee et al. | 435/6 |
| 7,045,756 | B2 * | 5/2006 | Kinney et al. | 250/208.1 |
| 7,067,819 | B2 * | 6/2006 | Janik | 250/372 |
| 7,135,143 | B2 * | 11/2006 | Abbott et al. | 422/82.05 |
| 7,222,025 | B2 * | 5/2007 | Weiner et al. | 702/27 |

(Continued)

OTHER PUBLICATIONS

Epstein et al., High-Density, Microsphere-Based Fiber Optic DNA Microarrays, 2003, Biosensors and Bioelectronics 18, pp. 541-546.*

*Primary Examiner*—John E Barlow, Jr.
*Assistant Examiner*—Toan M Le
(74) *Attorney, Agent, or Firm*—William R. McCarthy, III; Philip L. McGarrigle

(57) ABSTRACT

In one embodiment, a method of determining a drift value is described that includes performing one or more X-axis translations of an excitation beam over a probe array; measuring light responsive to the excitation beam from at least two positional reference elements associated with the probe array for the X-axis translations; calculating a distance value for the X-axis translation using a positional relationship of a known location associated with each of the positional reference elements and positions of the positional reference elements from the measured light; and determining a drift value using a difference between the calculated distance value and an expected distance value.

30 Claims, 7 Drawing Sheets

U.S. PATENT DOCUMENTS 7,317,415 B2 * 1/2008 Kaiser .................. 341/155
7,324,677 B2 * 1/2008 Minor .................. 382/129
2004/0012676 A1 * 1/2004 Weiner et al. ............ 348/207.1

* cited by examiner

SYSTEM, METHOD, AND COMPUTER PRODUCT FOR DETECTION INSTRUMENT CALIBRATION

RELATED APPLICATIONS

The present application claims priority from U.S. Provisional Patent Application Ser. No. 60/611,546, titled "System, Method, and Software Product for Detection Instrument Calibration", filed Sep. 20, 2004; which is hereby incorporated by reference herein in its entirety for all purposes.

BACKGROUND

1. Field of the Invention

The present invention relates to systems and methods for examining biological material. In particular, the invention relates to the calibration of optical readers or scanners for detecting emissions from biological probe arrays having small features that may be arranged in high densities on the arrays.

2. Related Art

Synthesized nucleic acid probe arrays, such as Affymetrix® GeneChip® probe arrays, and spotted probe arrays, have been used to generate unprecedented amounts of information about biological systems. For example, the GeneChip® Human Genome U133 Plus 2.0 probe array available from Affymetrix, Inc. of Santa Clara, Calif., is comprised of a single microarray containing over 1,000,000 unique oligonucleotide features covering more than 47,000 transcripts that represent more than 33,000 human genes. Analysis of expression data from such microarrays may lead to the development of new drugs and new diagnostic tools.

SUMMARY OF THE INVENTION

Systems, methods, and products to address these and other needs are described herein with respect to illustrative, non-limiting, implementations. Various alternatives, modifications and equivalents are possible. For example, certain systems, methods, and computer software products are described herein using exemplary implementations for analyzing data from arrays of biological materials such as, for instance, Affymetrix® GeneChip® probe arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates or media, which may include polymeric coatings or other layers on top of slides or other substrates. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

In one embodiment, a method of determining a drift value is described that comprises performing one or more X-axis translations of an excitation beam over a probe array; measuring light responsive to the excitation beam from at least two positional reference elements associated with the probe array for the X-axis translations; calculating a distance value for the X-axis translation using a positional relationship of a known location associated with each of the positional reference elements and positions of the positional reference elements from the measured light; and determining a drift value using a difference between the calculated distance value and an expected distance value.

A system for determining a drift value is also described that comprises a translation element that performs one or more X-axis translations of an excitation beam over a probe array; one or more detectors that measure light responsive to the excitation beam from at least two positional reference elements associated with the probe array for the X-axis translations; and a software application stored for execution is system memory of a computer that performs the method of: calculating a distance value for the X-axis translation using a positional relationship of a known location associated with each of the positional reference elements and positions of the positional reference elements from the measured light; and determining a drift value using a difference between the calculated distance value and an expected distance value.

In addition, a method of correcting X-axis error in a probe array image is described that comprises performing one or more X-axis translations of an excitation beam over a probe array; measuring light responsive to the excitation beam from at least two positional reference elements associated with the probe array for the X-axis translations; calculating a distance value for the X-axis translation using a positional relationship of a known location associated with each of the positional reference elements and positions of the positional reference elements from the measured light; determining a drift value using a difference between the calculated distance value and an expected distance value; and applying the drift value to a plurality of pixels of an image of a plurality of probe features acquired from the probe array.

Further, a probe array scanner for correcting X-axis error in a probe array image is described that comprises a probe array scanner that comprises; a translation element the performs one or more X-axis translations of an excitation beam over a probe array; one or more detectors that measure light responsive to the excitation beam from at least two positional reference elements associated with the probe array for the X-axis translations; and a software application stored for execution in system memory of a computer that performs the method of: calculating a distance value for the X-axis translation using a positional relationship of a known location associated with each of the positional reference elements and positions of the positional reference elements from the measured light; determining a drift value using a difference between the calculated distance value and an expected distance value; and applying the drift value to a plurality of pixels of an image of a plurality of probe features acquired from the probe array.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 100 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

DETAILED DESCRIPTION

Figure 1:
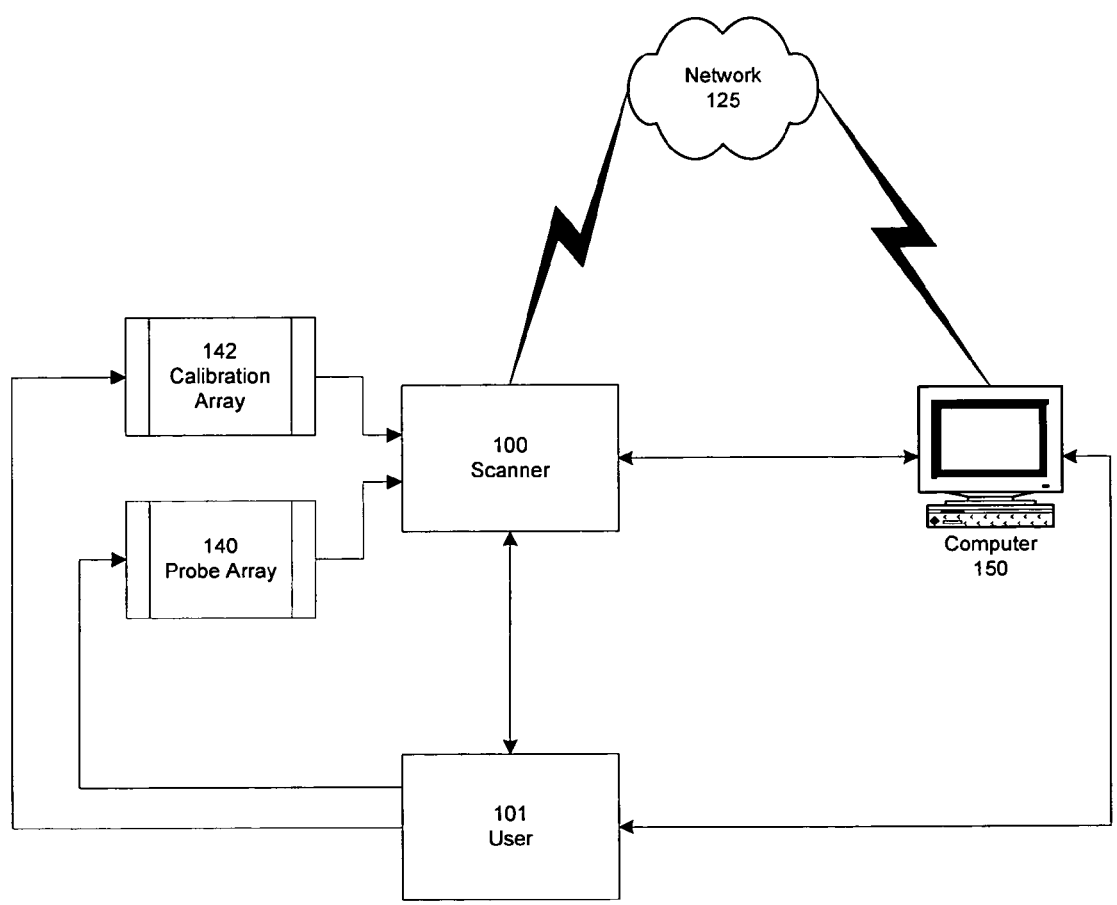
FIG. 1 is a functional block diagram of one embodiment of a scanner instrument enabled to scan a probe array and computer system for image acquisition and analysis.

The description below is designed to present specific embodiments and not to be construed as limiting in any way. Also, reference will be made to articles and patents to show general features that are incorporated into the present disclosure, but the invention is not limited by these descriptions. Many scanner designs may be used in order to detect emission signals appropriate for the acquisition of experimental data derived from probe array 140.

a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W.H. Freeman Pub., New York, N.Y. and Berg et al. (2002) Biochemistry, 5th Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841; WO 00/58516; U.S. Pat. Nos. 5,143,854; 5,242,974; 5,252,743; 5,324,633; 5,384,261; 5,405,783; 5,424,186; 5,451,683; 5,482,867; 5,491,074; 5,527,681; 5,550,215; 5,571,639; 5,578,832; 5,593,839; 5,599,695; 5,624,711; 5,631,734; 5,795,716; 5,831,070; 5,837,832; 5,856,101; 5,858,659; 5,936,324; 5,968,740; 5,974,164; 5,981,185; 5,981,956; 6,025,601; 6,033,860; 6,040,193; 6,090,555; 6,136,269; 6,269,846; and 6,428,752; in PCT Applications Nos. PCT/US99/00730 (International Publication No. WO 99/36760); and PCT/US01/04285 (International Publication No. WO 01/58593); which are all incorporated herein by reference in their entirety for all purposes.

Patents that describe synthesis techniques in specific embodiments include U.S. Pat. Nos. 5,412,087; 6,147,205; 6,262,216; 6,310,189; 5,889,165; and 5,959,098; which are all incorporated herein by reference in their entirety for all purposes. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992;

6,013,449; 6,020,135; 6,033,860; 6,040,138; 6,177,248; and 6,309,822. Genotyping and uses therefore are shown in U.S. Ser. Nos. 10/442,021; and U.S. Pat. Nos. 5,856,092; 6,300,063; 5,858,659; 6,284,460; 6,361,947; 6,368,799; 6,333,179; and 6,872,529. Other uses are embodied in U.S. Pat. Nos. 5,871,928; 5,902,723; 6,045,996; 5,541,061; and 6,197,506; which are all incorporated herein by reference in their entirety for all purposes.

The present invention also contemplates sample preparation methods in certain preferred embodiments. Prior to or concurrent with genotyping, the genomic sample may be amplified by a variety of mechanisms, some of which may employ PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202; 4,683,195; 4,800,159; 4,965,188; and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909; 5,861,245) and nucleic acid based sequence amplification (NABSA). (See, U.S. Pat. Nos. 5,409,818; 5,554,517; and 6,063,603, each of which is incorporated herein by reference). Other amplification methods that may be used are described in, U.S. Pat. Nos. 5,242,794; 5,494,810; 4,988,617; and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592, 6,632,611, and 6,872,529; and U.S. Ser. Nos. 09/916,135; and 09/920,491 (U.S. Patent Application Publication 20030096235).

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928; 5,874,219; 6,045,996; 6,386,749; and 6,391,623 each of which are incorporated herein by reference.

The present invention also contemplates signal detection of hybridization between ligands in certain preferred embodiments. For example, methods and apparatus for signal detection and processing of intensity data are disclosed in, U.S. Pat. Nos. 5,143,854; 5,547,839; 5,578,832; 5,631,734; 5,800,992; 5,834,758; 5,856,092; 5,902,723; 5,936,324; 5,981,956; 6,025,601; 6,090,555; 6,141,096; 6,171,793; 6,185,030; 6,201,639; 6,207,960; 6,218,803; 6,225,625; 6,252,236; 6,335,824; 6,403,320; 6,407,858; 6,472,671; 6,490,533; 6,650,411; and 6,643,015, in U.S. patent application Ser. Nos. 10/389,194; 10/913,102; and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROMIRAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,733,729; 5,593,839; 5,795,716; 5,733,729; 5,974,164; 6,066,454; 6,090,555; 6,185,561; 6,188,783; 6,223,127; 6,228,593; 6,229,911; 6,242,180; 6,308,170; 6,361,937; 6,420,108; 6,484,183; 6,505,125; 6,510,391; 6,532,462; 6,546,340; and 6,687,692.

Additionally, the present invention may have preferred embodiments that include methods for providing genetic information over networks such as the Internet as shown in U.S. Ser. Nos. 10/197,621; 10/063,559 (United States Publication Number 20020183936); 10/065,856; 10/065,868; 10/328,818; 10/328,872; 10/423,403; 10/903,344; and 10/903,641.

b) Definitions

The term "admixture" refers to the phenomenon of gene flow between populations resulting from migration. Admixture can create linkage disequilibrium (LD).

The term "allele" as used herein is any one of a number of alternative forms a given locus (position) on a chromosome. An allele may be used to indicate one form of a polymorphism, for example, a biallelic SNP may have possible alleles A and B. An allele may also be used to indicate a particular combination of alleles of two or more SNPs in a given gene or chromosomal segment. The frequency of an allele in a population is the number of times that specific allele appears divided by the total number of alleles of that locus.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "biopolymer" or sometimes refer by "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a biopolymer is a "biomonomer".

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified.

Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "effective amount" as used herein refers to an amount sufficient to induce a desired result.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotype" as used herein refers to the genetic information an individual carries at one or more positions in the genome. A genotype may refer to the information present at a single polymorphism, for example, a single SNP. For example, if a SNP is biallelic and can be either an A or a C then if an individual is homozygous for A at that position the genotype of the SNP is homozygous A or AA. Genotype may also refer to the information present at a plurality of polymorphic positions.

The term "Hardy-Weinberg equilibrium" (HWE) as used herein refers to the principle that an allele that when homozygous leads to a disorder that prevents the individual from reproducing does not disappear from the population but remains present in a population in the undetectable heterozygous state at a constant allele frequency.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na+], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip® Mapping Assay Manual, 2004.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991); LNAs, as described in Koshkin et al. Tetrahedron 54:3607-3630, 1998, and U.S. Pat. No. 6,268, 490; aptamers, and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage analysis" as used herein refers to a method of genetic analysis in which data are collected from affected families, and regions of the genome are identified that co-segregated with the disease in many independent families or over many generations of an extended pedigree. A disease locus may be identified because it lies in a region of the genome that is shared by all affected members of a pedigree.

The term "linkage disequilibrium" or sometimes referred to as "allelic association" as used herein refers to the preferential association of a particular allele or genetic marker with a specific allele, or genetic marker at a nearby chromosomal location more frequently than expected by chance for any particular allele frequency in the population. For example, if locus X has alleles A and B, which occur equally frequently, and linked locus Y has alleles C and D, which occur equally frequently, one would expect the combination AC to occur with a frequency of 0.25. If AC occurs more frequently, then alleles A and C are in linkage disequilibrium. Linkage disequilibrium may result from natural selection of certain combination of alleles or because an allele has been introduced into a population too recently to have reached equilibrium with linked alleles. The genetic interval around a disease locus may be narrowed by detecting disequilibrium between nearby markers and the disease locus. For additional information on linkage disequilibrium see Ardlie et al., Nat. Rev. Gen. 3:299-309, 2002.

The term "mendelian inheritance" as used herein refers to a set of commonly held principles that underlie the theories of genetic inheritance from parent to offspring that include units of inheritance that are passed intact from one generation to the next.

The term "lod score" or "LOD" is the log of the odds ratio of the probability of the data occurring under the specific hypothesis relative to the null hypothesis. LOD=log [probability assuming linkage/probability assuming no linkage].

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate.

The term "nucleic acids" as used herein may include a polymeric form of nucleotides of any length, any polymer or oligomer of pyrimidine and purine bases, preferably cytosine, thymine, and uracil, and adenine and guanine, respectively. See Albert L. Lehninger, Principles of Biochemistry, at 793-800 (Worth Pub. 1982). Indeed, the present invention contemplates any deoxyribonucleotide, ribonucleotide or peptide nucleic acid component (PNAs), other natural, chemically or biochemically modified, non-natural, or derivatized nucleotide bases and any chemical variants thereof, such as methylated, hydroxymethylated or glucosylated forms of these bases, and the like. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

c) Embodiments of the Present Invention

Embodiments of a scanning system are described herein that are enabled to accurately image features of a probe array that may include feature sizes in a range of 24 cm, 5 µm, 1 µm or smaller in a dimension (such as the side of a square, side of a rectangle, or diameter of a spot). Accurately imaging very small feature sizes generally requires that tolerances for error associated with the hardware and software elements of a scanning system be similarly small such as, for instance, allowable position error may not exceed +/−1 pixel of an acquired image. Due to a variety of factors, multiple pixels are generally collected for every feature; for example, a range of 4-144 pixels may be acquired for each feature depending upon the size of features associated with a particular implementation of probe array 140 and the pixel size associated with scanner hardware and software implementations.

Probe Array 140: An illustrative example of probe array 140 is provided in FIGS. 1, 2, and 3. Descriptions of probe arrays are provided above with respect to "Nucleic Acid Probe arrays" and other related disclosure. In various implementations probe array 140 may be disposed in a cartridge or housing such as, for example, the GeneChip® probe array available from Affymetrix, Inc. of Santa Clara Calif. Additional examples of probe arrays and associated cartridges or housings may be found in U.S. Pat. Nos. 5,945,334, 6,287, 850, 6,399,365, 6,551,817, each of which is hereby incorporated by reference herein in its entirety for all purposes.

Scanner 100: Labeled targets hybridized to probe arrays may be detected using various devices, sometimes referred to as scanners, as described above with respect to methods and apparatus for signal detection. An illustrative device is shown in FIG. 1 as scanner 100, and in greater detail in FIG. 2 that for instance includes scanner optics and detectors 200. For example, scanners image the targets by detecting fluorescent or other emissions from labels associated with target molecules, or by detecting transmitted, reflected, or scattered radiation. A typical scheme employs optical and other elements to provide excitation light and to selectively collect the emissions.

For example, scanner 100 provides a signal representing the intensities (and possibly other characteristics, such as color that may be associated with a detected wavelength) of the detected emissions or reflected wavelengths of light, as well as the locations on the substrate where the emissions or reflected wavelengths were detected. Typically, the signal includes intensity information corresponding to elemental sub-areas of the scanned substrate. The term "elemental" in this context means that the intensities, and/or other characteristics, of the emissions or reflected wavelengths from this area each are represented by a single value. When displayed as an image for viewing or processing, elemental picture elements, or pixels, often represent this information. Thus, in the present example, a pixel may have a single value representing the intensity of the elemental sub-area of the substrate from which the emissions or reflected wavelengths were scanned. The pixel may also have another value representing another characteristic, such as color, positive or negative image, or other type of image representation. The size of a pixel may vary in different embodiments and could include a pixel size of >2.5 µm, 2.5 cm, 1.5 µm, 1.0 µm, or sub-micron pixel size. Two examples where the signal may be incorporated into data are data files in the form *.dat or *.tif as generated respectively by Affymetrix® Microarray Suite (described in U.S. patent application Ser. No. 10/219,882, which is hereby incorporated by reference herein in its entirety for all purposes) or Affymetrix® GeneChip® Operating Software based on images scanned from GeneChip® arrays, and Affymetrix® Jaguar™ software (described in U.S. patent application Ser. No. 09/682,071, which is hereby incorporated by reference herein in its entirety for all purposes) based on images scanned from spotted arrays. Examples of scanner systems that may be implemented with embodiments of the present invention include U.S. patent application Ser. Nos. 10/389,194; and 10/913,102, both of which are incorporated by reference above; U.S. patent application Ser. No. 10/846, 261, titled "System, Method, and Product for Providing A Wavelength-Tunable Excitation Beam", filed May 13, 2004; and U.S. Provisional Patent Application Ser. No. 60/623,390, titled "System, Method and Product for Multiple Wavelength Detection Using Single Source Excitation", filed Oct. 29, 2004, which is hereby incorporated by reference herein in its entirety for all purposes.

Computer 150: An illustrative example of computer 150 is provided in FIG. 1 and also in greater detail in FIG. 2. Computer 150 may be any type of computer platform such as a workstation, a personal computer, a server, or any other present or future computer. Computer 150 typically includes known components such as a processor 255, an operating system 260, system memory 270, memory storage devices 281, and input-output controllers 275, input devices 240, and display/output devices 245. Display/Output Devices 245 may include display devices that provides visual information, this information typically may be logically and/or physically organized as an array of pixels. A Graphical user interface (GUI) controller may also be included that may comprise any of a variety of known or future software programs for providing graphical input and output interfaces such as for instance GUI's 246. For example, GUI's 246 may provide one or more graphical representations to a user, such as user 101, and also be enabled to process user inputs via GUI's 246 using means of selection or input known to those of ordinary skill in the related art.

It will be understood by those of ordinary skill in the relevant art that there are many possible configurations of the components of computer 150 and that some components that may typically be included in computer 150 are not shown, such as cache memory, a data backup unit, and many other devices. Processor 255 may be a commercially available processor such as an Itanium® or Pentium® processor made by Intel Corporation, a SPARC® processor made by Sun Microsystems, an Athalon™ or Opteron™ processor made by AMD corporation, or it may be one of other processors that are or will become available. Processor 255 executes operating system 260, which may be, for example, a Windows®-type operating system (such as Windows NT® 4.0 with SP6a, or Windows® XP with SP2) from the Microsoft Corporation; a Unix® or Linux-type operating system available from many vendors or what is referred to as an open source; another or a future operating system; or some combination thereof. Operating system 260 interfaces with firmware and hardware in a well-known manner, and facilitates processor 255 in coordinating and executing the functions of various computer programs that may be written in a variety of programming languages. Operating system 260, typically in cooperation with processor 255, coordinates and executes functions of the other components of computer 150. Operating system 260 also provides scheduling, input-output control, file and data management, memory management, and communication control and related services, all in accordance with known techniques.

System memory 270 may be any of a variety of known or future memory storage devices. Examples include any commonly available random access memory (RAM), magnetic medium such as a resident hard disk or tape, an optical medium such as a read and write compact disc, or other memory storage device. Memory storage devices 281 may be any of a variety of known or future devices, including a compact disk drive, a tape drive, a removable hard disk drive, USB drive, or a diskette drive. Such types of memory storage devices 281 typically read from, and/or write to, a program storage medium (not shown) such as, respectively, a compact disk, magnetic tape, removable hard disk, USB drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 270 and/or the program storage device used in conjunction with memory storage device 281.

In some embodiments, a computer program product is described comprising a computer usable medium having control logic (computer software program, including program code) stored therein. The control logic, when executed by processor 255, causes processor 255 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 275 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 275 could include controllers for any of a variety of known display devices for presenting information to a user, whether a human or a machine, whether local or remote. In the illustrated embodiment, the functional elements of computer 150 communicate with each other via system bus 290. Some of these communications may be accomplished in alternative embodiments using network or other types of remote communications.

Figure 2:
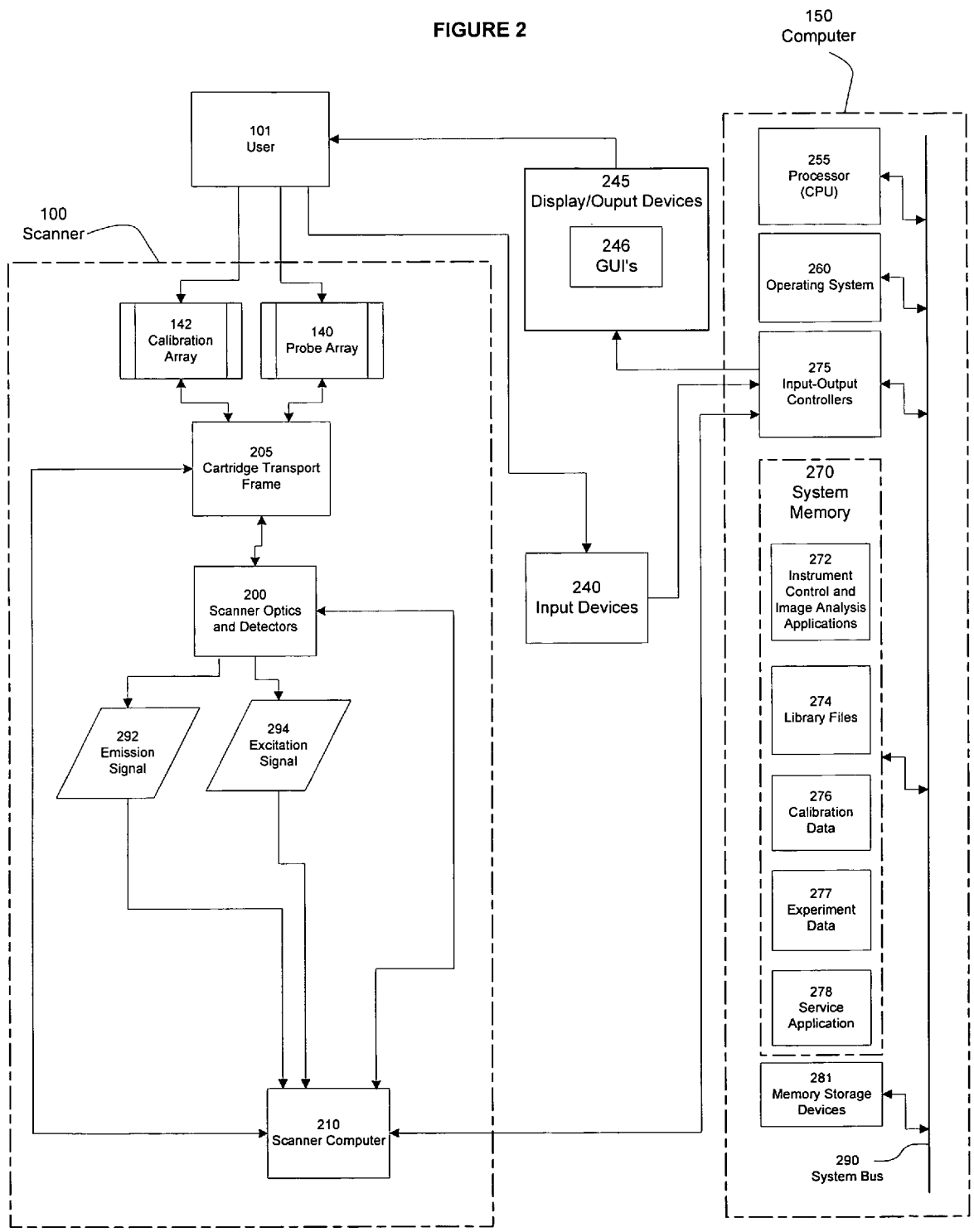
FIG. 2 is a functional block diagram of one embodiment of the scanner-computer system of FIG. 1, including a cartridge transport frame, scanner optics and detectors, and a scanner computer.

As will be evident to those skilled in the relevant art, instrument control and image processing applications 272, if implemented in software, may be loaded into and executed from system memory 270 and/or memory storage device 281. All or portions of applications 272 may also reside in a read-only memory or similar device of memory storage device 281, such devices not requiring that applications 272 first be loaded through input-output controllers 275. It will be understood by those skilled in the relevant art that applications 272, or portions of it, may be loaded by processor 255 in a known manner into system memory 270, or cache memory (not shown), or both, as advantageous for execution. Also illustrated in FIG. 2 are library files 274, calibration data 276, and experiment data 277 stored in system memory 270. For example, calibration data 276 could include one or more values or other types of calibration data related to the calibration of scanner 100 or other instrument. Additionally, experiment data 277 could include data related to one or more experiments or assays such as the excitation ranges or values associated with one or more fluorescent labels.

Network 125 may include one or more of the many various types of networks well known to those of ordinary skill in the art. For example, network 125 may include what is commonly referred to as a TCP/IP network, or other type of network that may include the internet, or intranet architectures.

Instrument control and image processing applications 272: Instrument control and image processing applications 272 may be any of a variety of known or future image processing applications. Examples of applications 272 include Affymetrix® Microarray Suite, Affymetrix® GeneChip® Operating Software (hereafter referred to as GCOS), and Affymetrix® Jaguar™ software, noted above. Applications 272 may be loaded into system memory 270 and/or memory storage device 281 through one of input devices 240.

Embodiments of applications 272 include executable code being stored in system memory 270 of an implementation of computer 150. Applications 272 may provide a single interface for both the client workstation and one or more servers such as, for instance, GeneChip® Operating Software Server (GCOS Server). Applications 272 could additionally provide the single user interface for one or more other workstations and/or one or more instruments. In the presently described implementation, the interface may communicate with and control one or more elements of the one or more servers, one or more workstations, and the one or more instruments. In the described implementation the client workstation could be located locally or remotely to the one or more servers and/or one or more other workstations, and/or one or more instruments. The interface may, in the present implementation, include an interactive graphical user interface that allows a user to make selections based upon information presented in the GUI. For example, applications 272 may provide an interactive GUI that allows a user to select from a variety of options including data selection, experiment parameters, calibration values, probe array information. Applications 272 may also provide a graphical representation of raw or processed image data where the processed image data may also include annotation information superimposed upon the image such as, for instance, base calls, features of the probe array, or other useful annotation information. Further examples of providing annotation information on image data are provided in U.S. Provisional Patent Application Ser. No. 60/493,950, titled "System, Method, and Product for Displaying Annotation Information Associated with Microarray Image Data", filed Aug. 8, 2003, which is hereby incorporated by reference herein in its entirety for all purposes.

In alternative implementations, applications 272 may be executed on a server, or on one or more other computer platforms connected directly or indirectly (e.g., via another network, including the Internet or an Intranet) to network 125.

Embodiments of applications 272 also include instrument control features. The instrument control features may include the control of one or more elements of one or more instruments that could, for instance, include elements of a fluidics station, what may be referred to as an autoloader, and scanner 100. The instrument control features may also be capable of receiving information from the one more instruments that could include experiment or instrument status, process steps, or other relevant information. The instrument control features could, for example, be under the control of or an element of the interface. In the present example, a user may input desired control commands and/or receive the instrument control information via one of GUI's 246. Additional examples of instrument control via a GUI or other interface is provided in U.S. patent application Ser. No. 10/764,663, titled "System, Method and Computer Software Product for Instrument Control, Data Acquisition, Analysis, Management and Storage", filed Jan. 26, 2004, which is hereby incorporated by reference herein in its entirety for all purposes.

In some embodiments, image data is operated upon by applications 272 to generate intermediate results. Examples of intermediate results include so-called cell intensity files (*.cel) and chip files (*.chp) generated by Affymetrix® GeneChip® Operating Software or Affymetrix® Microarray Suite (as described, for example, in U.S. patent application Ser. Nos. 10/219,882, and 10/764,663, both of which are hereby incorporated herein by reference in their entireties for all purposes) and spot files (*.spt) generated by Affymetrix® Jaguar™ software (as described, for example, U.S. Pat. Nos. 6,789,040, 6,829,376, in PCT Application PCT/US01/26390 and in U.S. patent application Ser. Nos. 09/682,071, and 09/682,076, all of which are hereby incorporated by reference herein in their entireties for all purposes). For convenience, the term "file" often is used herein to refer to data generated or used by applications 272 and executable counterparts of other applications, but any of a variety of alternative techniques known in the relevant art for storing, conveying, and/or manipulating data may be employed.

For example, applications 272 receives image data derived from a GeneChip® probe array and generates a cell intensity file. This file contains, for each probe feature scanned by scanner 100, a single value representative of the intensities of pixels measured by scanner 100 for that probe feature. Thus, for instance each value is representative of the presence or absence of tagged or labeled target molecules present in the sample that hybridized to the corresponding probe feature. Many probe molecules complementary to each target molecule may be present in each probe feature, as a probe feature on a GeneChip® probe array may include, for example, millions of oligonucleotides designed to detect the target molecules.

As noted, another file illustratively assumed to be generated by applications 272 is a chip file. In the present example, in which applications 272 include Affymetrix® GeneChip® Operating Software, the chip file is derived from analysis of the cell file combined in some cases with information derived from lab data and/or library files 274 that specify details regarding the sequences and locations of probes and controls. The resulting data stored in the chip file includes degrees of hybridization, absolute and/or differential (over two or more experiments) expression, genotype comparisons, detection of polymorphisms and mutations, and other analytical results.

In another example, in which applications 272 includes Affymetrix® Jaguar™ software operating on image data from a spotted probe array, the resulting spot file includes the intensities of labeled targets that hybridized to probes in the array. Further details regarding cell files, chip files, and spot files are provided in U.S. Pat. No. 6,789,040 incorporated by reference above, as well as Ser. No. 10/126,468; and Ser. No. 09/682,098; which are hereby incorporated by reference herein in their entireties for all purposes. As will be appreciated by those skilled in the relevant art, the preceding and following descriptions of files generated by applications 272 are exemplary only, and the data described, and other data, may be processed, combined, arranged, and/or presented in many other ways.

User 101 and/or automated data input devices or programs (not shown) may provide data related to the design or conduct of experiments. As one further non-limiting example related to the processing of an Affymetrix® GeneChip® probe array, the user may specify an Affymetrix catalogue or custom chip type (e.g., Human Genome U133 plus 2.0 chip) either by selecting from a predetermined list presented by GCOS or by scanning a bar code, RFID label, magnetic strip, or other means of electronic identification related to a chip to read its type. GCOS may associate the chip type with various scanning parameters stored in data tables including the area of the chip that is to be scanned, the location of chrome borders on the chip used for auto-focusing, the wavelength or intensity of laser light to be used in reading the chip, and so on. As noted, applications 272 may apply some of this data in the generation of intermediate results. For example, information about the dyes may be incorporated into determinations of relative expression.

Those of ordinary skill in the related art will appreciate that one or more operations of applications 272 may be performed by software or firmware associated with various instruments. For example, scanner 100 could include a computer that may include a firmware component that performs or controls one or more operations associated with scanner 100, such as for instance scanner computer 210 and scanner firmware 472.

Figure 3:
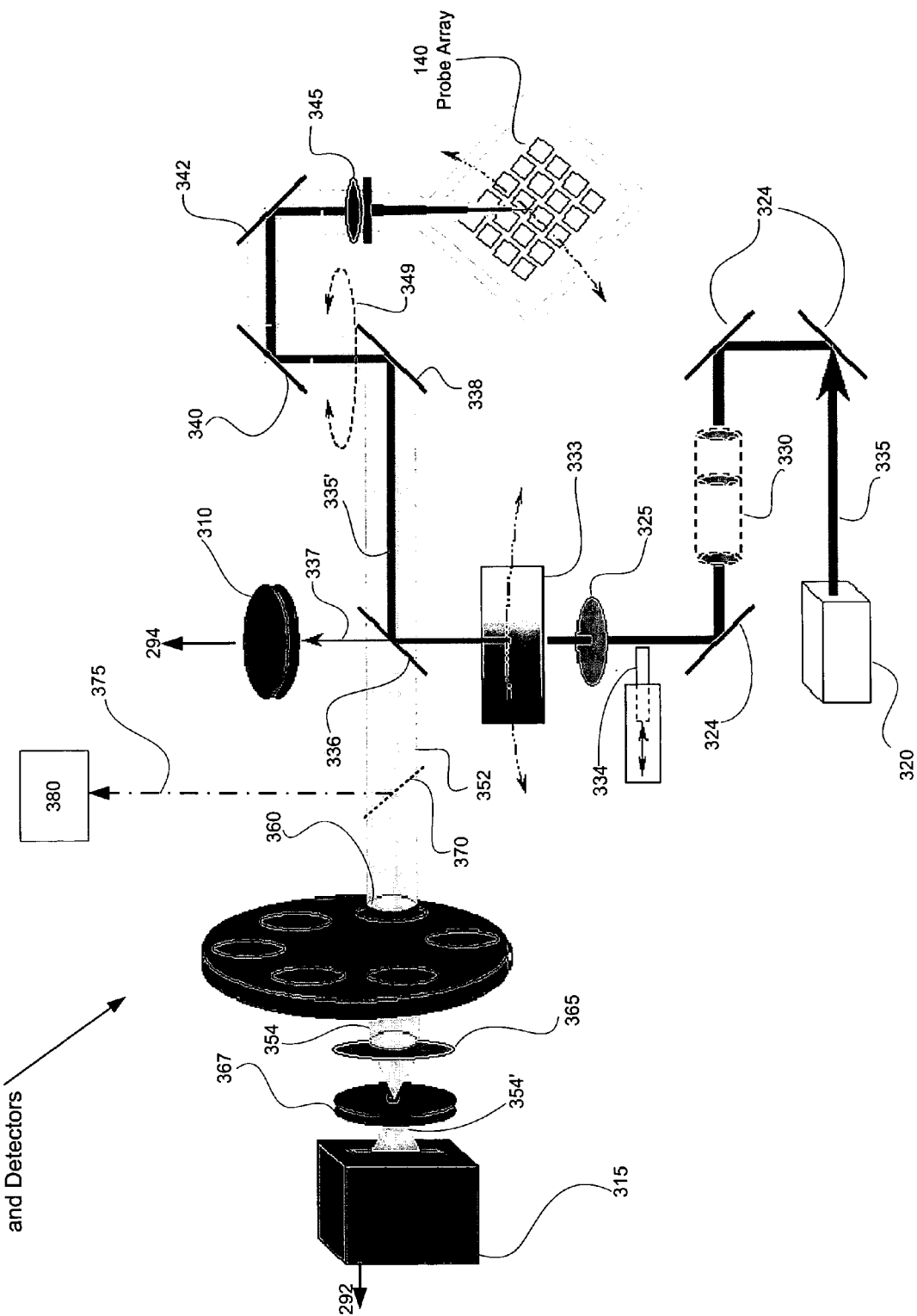
FIG. 3 is a simplified graphical representation of the scanner optics and detectors of FIG. 2, suitable for providing excitation light and the detection of emission signals.

Scanner Optics and Detectors 200: FIG. 3 provides a simplified graphical example of possible embodiments of optical elements associated with scanner 100, illustrated as scanner optics and detectors 200. For example, an element of the presently described invention includes source 320 that could include a laser such as, for instance, a solid state, diode pumped, frequency doubled Nd: YAG (Neodymium-doped Yttrium Aluminum Garnet) or YVO4 laser producing green laser light, having a wavelength of 532 nm or other laser implementation. In the present example, source 320 provides light within the excitation range of one or more fluorescent labels associated with target molecules hybridized to probes disposed on probe array 140 or fluorescent labels associated with a calibration standard. Also in the present example, the wavelength of the excitation light provided by source 320 may be tunable such to enable the use multiple color assays (i.e. employing multiple fluorescent labels with distinct ranges of excitation and emission wavelengths) associated with an embodiment of probe array 140 (Further examples of tunable sources are described in U.S. patent application Ser. No. 10/846,261, titled "System, Method, and Product for Providing a Wavelength-Tunable Excitation Beam, filed May 13, 2004, which is hereby incorporated by reference above). Those of ordinary skill in the related art will appreciate that other types of sources 320 may be employed in the present invention such as incandescent sources, one or more light emitting diodes (sometime referred to as LED's), halogen or xenon sources, metal halide sources, or other sources known in the art.

In some embodiments, a single implementation of source 320 is employed that produces a single excitation beam, illustrated in FIG. 3 as excitation beam 335. Alternative embodiments may include multiple implementations of source 320 that each provide excitation light that may be combined into a single beam or directed along separate optical paths to a target, although those of ordinary skill in the related art will appreciate that there are several advantages to implementing a single source over multiple sources such as complexity, space, power consumption, heat, and expense. For example, source 320 may include at least one tunable laser to provide a selectable wavelength of light that, for example, may be varied by applications 272 or other software or firmware implementation during a scanning operation or for successive scan operations. In the present example, it may be desirable in some implementations to provide multiple wavelengths of light during the acquisition of each pixel of image data, where the excitation wavelength may be dynamically changed during the pixel acquisition period. Application 272 or Firmware 472 may process the acquired pixel data and associate each known excitation wavelength during the period with received emissions to produce an unambiguous image of the fluorescent labels present.

In another example, one or more elements or methods may be employed to tune the wavelength of excitation beam 335 produced by source 320 to correspond to the excitation wavelengths of each of multiple fluorophores having a different range of excitation spectra. In the present example, a probe array experiment may comprise the use of two fluorophores that have different excitation wavelength properties, where each excitation wavelength is associated with a particular emission wavelength. Scanner 100 may tune excitation beam 335 to correspond to the excitation wavelength of the first fluorophore, and perform a complete scan. In the present example, excitation beam 335 is then tuned to the excitation wavelength of the second fluorophore and probe array 140 is completely scanned again. The process may be repeated for each fluorophore used in the experiment. Those of ordinary skill in the related art will appreciate that the risk of photobleaching fluorophores is low based, at least in part, upon the degree of difference between excitation spectra associated with each fluorophore. The term "photobleaching" as used herein generally refers to a characteristic of some fluorescent molecules where the amount of emitted light is dependant upon the amount of time that a fluorophore is exposed to the excitation light. The length of time of exposure to the excitation wavelengths corresponds to a reduction in emission intensity from the fluorescent molecule until it is reduced to a value that may be zero.

Further references herein to source 320 generally will assume for illustrative purposes that they are lasers, but, as noted, other types of sources, e.g., x-ray sources, light emitting diodes, incandescent sources, or other electromagnetic sources may be used in various implementations. The Handbook of Biological Confocal Microscopy (James B. Pawley, ed.) (2.ed.; 1995; Plenum Press, NY), includes information known to those of ordinary skill in the art regarding the use of lasers and associated optics, is hereby incorporated herein by reference in its entirety.

FIG. 3 further provides an illustrative example of the paths of excitation beam 335 and emission beam 352 and a plurality of optical components that comprise scanner optics 200. In the present example, excitation beam 335 is emitted from source 320 and is directed along an optical path by one or more turning mirrors 324 toward a three-lens beam conditioner/expander 330. Turning mirrors are commonly associated with optical systems to provide the necessary adjustments to what may be referred to as the optical path such as, for instance, to allow for alignment of excitation beam 335 at objective lens 345 and to allow for alignment of emission beam 354 at detector 315. For example, turning mirrors 324 also serve to "fold" the optical path into a more compact size & shape to facilitate overall scanner packaging. The number of turning mirrors 324 may vary in different embodiments and may depend on the requirements of the optical path. In some embodiments it may be desirable that excitation beam 335 has a known diameter. Beam conditioner/expander 330 may provide one or more optical elements that adjust a beam diameter to a value that could, for instance, include a diameter of 1.076 mm±10%. For example, the one or more optical elements could include a three-lens beam expander that may increase the diameter of excitation beam 335 to a desired value. Alternatively, the one or more optical elements may reduce the diameter of excitation beam 335 to a desired value. Additionally, the one or more optical elements of beam conditioner/expander 330 may further condition one or more properties of excitation beam 335 to provide other desirable characteristics, such as providing what those of ordinary skill in the related art refer to as a plane wavefront to objective lens 345. Excitation beam 335 with the desirable characteristics may then exit beam conditioner/expander 330 and continue along the optical path that may again be redirected by one or more turning mirrors 324 towards excitation filter 325.

Filter 325 may be used to remove or block light at wavelengths other than excitation wavelengths, and generally need not be included if, for example, source 320 does not produce light at these extraneous wavelengths. However, it may be desirable in some applications to use inexpensive sources and often it is cheaper to filter out-of-mode light than to design the source to avoid producing such extraneous emissions. In some embodiments, filter 325 allows all or a substantial portion of light at one or more excitation wavelengths to pass through without affecting other characteristics of excitation beam 335, such as the desirable characteristics modified by beam conditioner/expander 330. Also, a plurality of filters 325 may also be associated with a filter wheel or other means for selectively translating a desired filter in the optical path. For example, where excitation beam 335 is tunable to a variety of desired wavelengths as described above it may be desirable to translate an implementation of filter 325 into the optical path of excitation bean 335 that is associated with the particular wavelength.

After exiting filter 325 excitation beam 335 may then be directed along the optical path to laser attenuator 333. Laser attenuator 333 may provide a means for adjusting the level of power of excitation beam 335. In some embodiments, attenuator 333 may, for instance, be comprised of a variable neutral density filter. Those of ordinary skill in the related art will appreciate that neutral density filters, such as absorptive, metallic, or other type of neutral density filter, may be used for reducing the amount of light that is allowed to pass through. The amount of light reduction may depend upon what is referred to as the density of the filter, for instance, as the density increases the amount of light allowed to pass through decreases. The neutral density filter may additionally include a density gradient. For example, the presently described embodiment may include laser attenuator 333 that includes a neutral density filter with a density gradient. Attenuator 333, acting under the control of applications 272 and/or firmware 472 may use a step motor that alters the position of the neutral density filter with respect to the optical path. The neutral density filter thus reduces the amount of light allowed to pass through based, at least in part, upon the position of the filter gradient relative to the optical path. In the present example, the power level of excitation beam is measured by laser power monitor 310 that is described further below, and may be dynamically adjusted to a desired level.

Some embodiments may include one or more implementations of shutter 334. Some implementations may include positioning shutter 334 in one or more locations within scanner 100, along the optical path such that shutter 334 provides a means to block all laser light from reaching probe array 140, and in some implementations additionally blocking all laser light from reaching laser power monitor 310. Shutter 334 may use a variety of means to completely block the light beam. For example shutter 334 may use a motor under the control of applications 272 and/or firmware 472 to extend/retract a solid barrier that could be constructed of metal, plastic, or other appropriate material capable of blocking essentially all of excitation beam 335. Shutter 334 may be used for a variety of purposes such as, for example, for blocking all light from impinging on one or more photo detectors or monitors, including detector 315 and laser power monitor 310. In the present example, blocking the light may be used for calibration methods that measure and make adjustments to what is referred to as the "dark current" or background noise of the photo detectors.

Components of scanner optics and detectors 200 placed in the optical path after elements such as attenuator 333 and/or shutter 334 may also include dichroic beam splitter 336. Those of ordinary skill in the related art will appreciate that a dichroic beam splitter, also commonly referred to as a dichroic mirror, may include an optical element that is highly reflective to light of a certain wavelength range, and allow transmission of light through the beam splitter or mirror at one or more other wavelength ranges. In some embodiments, beam splitter 336 could also include what is referred to as a geometric beam splitter where a portion of the surface of beam splitter 336 is reflective to all light or light within a particular range of wavelengths, and the remaining portion is permissive to the light. Alternatively, the beam splitter or mirror may reflect a certain percentage of light at a particular wavelength and allow transmission of the remaining percentage. For example, dichroic beam splitter 336 may direct most of the excitation beam, illustrated as excitation beam 335', along an optical path towards objective lens 345 while allowing the small fractional portion of excitation beam 335 that is not reflected to pass through beam splitter 336, illustrated in FIG. 3 as partial excitation beam 337. In the present example, partial excitation beam 337 passes through dichroic beam splitter 336 to laser power monitor 310 for the purpose of measuring the power level of excitation beam 335 and providing feedback to applications 272 and/or firmware 472. Applications 272 and/or firmware 472 may then make adjustments, if necessary, to the power level via laser attenuator 333 as described above.

Monitor 310 may be any of a variety of conventional devices for detecting partial excitation beam 337, such as a silicon detector for providing an electrical signal representative of detected light, a photodiode, a charge-coupled device, a photomultiplier tube, or any other detection device for providing a signal indicative of detected light that is now available or that may be developed in the future. As illustrated in FIG. 3, detector 310 generates excitation signal 294 that represents the detected signal from partial excitation beam 337. In accordance with known techniques, the amplitude, phase, or other characteristic of excitation signal 294 is designed to vary in a known or determinable fashion depending on the power of excitation beam 335. The term "power" in this context refers to the capability of beam 335 to evoke emissions. For example, the power of beam 335 typically may be measured in milliwatts of laser energy with respect to the illustrated example in which the laser energy evokes a fluorescent signal. Thus, excitation signal 294 includes values that represent the power of beam 335 during particular times or time periods. Applications 272 and/or firmware 472 may receive signal 294 for evaluation and, as described above, if necessary make adjustments.

After reflection from beam splitter 336, excitation beam 335' may continue along an optical path that is directed via periscope mirror 338, turning mirror 340, and arm end turning mirror 342 to objective lens 345. In the illustrated implementation mirrors 338, 340, and 342 may have the same reflective properties as turning mirrors 324, and could, in some implementations, be used interchangeably with turning mirrors 324.

Lens 345 in the illustrated implementation may include a small, light-weight lens located on the end of an arm that is driven by a galvanometer around an axis perpendicular to the plane represented by galvo rotation 349. In one embodiment, lens 345 focuses excitation beam 335' down to a specified spot size at the best plane of focus that could, for instance, include a 3.5 cm spot size. Galvo rotation 349 results in objective lens 345 moving in an arc over a substrate, providing what may be referred to as an arcuate path that may also be referred to herein as a "scanning line", upon which biological materials typically have been synthesized or have been deposited. The arcuate path may, for instance, move in a 36 degree arc over a substrate. One or more fluorophores associated with the biological materials emit emission beam 352 at characteristic wavelengths in accordance with well-known principles. The term "fluorophore" commonly refers to a molecule that produces fluorescent light by energy transfer from light, chemical, or other types of energy sources.

Emission beam 352 in the illustrated example follows the reverse optical path as described with respect to excitation beam 335 until reaching dichroic beam splitter 336. In accordance with well known techniques and principles, the characteristics of beam splitter 336 are selected so that beam 352 (or a portion of it) is transmitted through the mirror rather than being reflected. Emission beam 352 is then directed along a desired optical path to filter wheel 360.

In one embodiment, filter wheel 360 may be provided to filter out spectral components of emission beam 352 that are outside of the emission band of one or more particular fluorophores. The emission band is determined by the characteristic emission frequencies of those fluorophores that are responsive to the frequency of excitation beam 335. Thus, for example, excitation beam 335 from source 320 excites certain fluorophores to a much greater degree than others. The result may include filtered emission beam 354 that is a representation of emission beam 352 that has been filtered by a desired filter of filter wheel 360.

In some implementations filter wheel 360 is capable of holding a plurality of filters that each could be tuned to different wavelengths corresponding to the emission spectra from different fluorophores. Filter wheel 360 may include a mechanism for turning the wheel to position a desired filter in the optical path of emission beam 352. The mechanism may include a motor or some other device for turning or translation that may be responsive to instructions from application 272 and/or firmware 472. For example, biological probe array experiments could be carried out on the same probe array where a plurality of fluorophores with different excitation and emission spectra are used that could be excited by a single source with tunable wavelengths or multiple sources. Additionally, multiple fluorescent dyes could be used that have the same excitation wavelengths but have differing emission spectral properties could be produced by methods such as those known to those in the art as fluorescent resonant energy transfer (FRET), or semiconductor nanocrystals (sometimes referred to as Quantum Dots). For example, FRET may be achieved when there are two fluorophores associated with the same target molecule. The emission wavelength of one fluorophore overlaps the excitation wavelength of the second fluorophore and results in the emission of a wavelength from the second fluorophore that is atypical of the class of fluorophores that use that excitation wavelength. As an alternative example, multiple embodiments of the quantum dots referred to above may be employed where each species of quantum dot may be tuned to excite at a common wavelength for all species but each species emits at a distinctive wavelength (Additional examples provided in U.S. Provisional Patent Application Ser. No. 60/623,390, incorporated by reference above). Thus by using an excitation beam of a single wavelength it is possible to obtain distinctly different emissions so that different features of a probe array could be labeled in a single experiment.

For example probe array 103 could be scanned using a filter of one wavelength, then one or more additional scans could be performed that each correspond to a particular fluorophore and filter pair. Instrument control and image processing applications 272 could then process the data so that the user could be presented with a single image or other format for data analysis.

In other implementations, multiple excitation sources 320 (or one or more adjustable-wavelength excitation sources) and corresponding multiple optical elements in optical paths similar to the illustrated one could be employed for simultaneous scans at multiple wavelengths. Other examples of scanner systems that utilize multiple emission wavelengths are described in U.S. Pat. No. 6,490,533, titled "System, Method, and Product For Dynamic Noise Reduction in Scanning of Biological Materials", filed Dec. 3, 2001; U.S. Pat. No. 6,650,411, titled "System, Method, and Product for Pixel Clocking in Scanning of Biological Materials", filed Dec. 3, 2001; and U.S. Pat. No. 6,643,015, titled "System, Method, and Product for Symmetrical Filtering in Scanning of Biological Materials", filed Dec. 3, 2001 each of which are hereby incorporated by reference in their entireties for all purposes.

In accordance with techniques well known to those of ordinary skill in the relevant arts, including that of confocal microscopy, beam 354 may be focused by various optical elements such as lens 365 and passed through illustrative pinhole 367, aperture, or other element. In accordance with known techniques, pinhole 367 is positioned such that it rejects light from focal planes other than the plane of focus of objective lens 345 (i.e., out-of-focus light), and thus increases the resolution of resulting images.

In some embodiments, pinhole 367 may be bi-directionally moveable along the optical path. As those of ordinary skill in the related art will appreciate, the appropriate placement of pinhole 367 to reject out of focus light is dependant upon the wavelength of emitted beam 354. Pinhole 367 may be movable via a motor or other means under the control of applications 272 and/or firmware 472 to a position that corresponds to the emission wavelength of the fluorophore being scanned. In the same or alternative embodiments, pinhole 367 may comprise a sufficiently large diameter to accommodate the emission wavelengths of several fluorophores if those wavelengths are relatively similar to each other. Also, some embodiments of pinhole 367 may include an "iris" type of aperture that expands and contracts so that the diameter of the hole or aperture is sufficient to permit the desired wavelength of light at the plane of focus to pass through while rejecting light that is substantially out of focus. Alternatively, a series of pinholes 367 may be utilized. For example, there may be an implementation of pinhole 367 associated with each fluorophore used with a biological probe array. Each implementation of pinhole 367 may be placed in the appropriate position to reject out of focus light corresponding to the emission wavelength of its associated fluorophore. Each of pinholes 367 may be mounted on a translatable stage, rotatable axis, or other means to move pinhole 367 in and out of the optical path. In the present example, the implementation of pinhole 367 corresponding to the fluorophore being scanned is positioned in the optical path under the control of applications 285, while the other implementations of pinhole 367 are positioned outside of the optical path thus allowing the implementation of pinhole 367 in the optical path to reject out of focus light. Also, some embodiments may include a lens that corrects for chromatic aberration associated with different emission wavelengths so that, for instance, the focal point associated with each wavelength is focused at a stationary pinhole.

After passing through pinhole 367, the portion of filtered emission beam 354 that corresponds to the plane of focus, represented as filtered emission beam 354', continues along a desired optical path and impinges upon detector 315.

Similar to excitation detector 310, emission detector 315 may be a silicon detector for providing an electrical signal representative of detected light, or it may be a photodiode, a charge-coupled device, a photomultiplier tube, or any other detection device that is now available or that may be developed in the future for providing a signal indicative of detected light. Detector 315 generates emission signal 292 that represents filtered emission beam 354' in the manner noted above with respect to the generation of excitation signal 294 by detector 310. Signal 292 and excitation signal 294 may be provided to applications 272 and/or firmware 472 for processing, as previously described.

Cartridge Transport frame 205: Another element of scanner 100 includes cartridge transport frame 205 that provides all of the degrees of freedom required to manipulate probe array 140 for the purposes of auto-focus, scanning, and calibration operations. Those of ordinary skill in the related art will appreciate that the term "degrees of freedom" generally refers to the number of independent parameters required to specify the position and orientation of an object. For example, in one embodiment, probe array 140 may be surrounded or encased by a housing that for instance could include a cartridge with a clear window for optical access to probe array 140. In the present example the cartridge could include one or more features such as a tab or keyed element that interfaces with transport frame 205 and defines the positional relationship of frame 205 and the cartridge. Frame 205 may then manipulate the position of the cartridge relative to one or more elements of scanner 100 such as, for instance, objective lens 345.

In one embodiment, transport frame 205 is capable of manipulating the cartridge in four of six possible degrees of freedom such as, for example, what may be generally referred to as roll, pitch, Z and Y. In the present example, it generally may not be necessary to manipulate a cartridge in the yaw or X axes, but may be possible in some alternative embodiments.

Probe array 140 may be brought into best focus by adjusting the distance of probe array 140 from objective lens 345. In some implementations, the distance adjustment may be employed by moving the position of one or more elements of transport frame 205, such as a focus stage, in the Z axis For example, movement of the focus stage in the Z axis may be actuated by one or more motors in a first direction that may decrease the distance between probe array 140 and objective lens 345, as well as the opposite direction that may increase the distance.

Translation of probe array 140 along the Y-axis may in one embodiment be accomplished by a precision linear stage, coupled to what is referred to as a micro-stepped motor/driver, open loop drive mechanism or other type of motorized mechanism. The linear stage may include a guide element to support and guide the housing or cartridge and additional elements to secure the housing or cartridge during scanner operation. In some embodiments, the linear stage may include independent position adjustment mechanisms enabled to adjust the position of probe array 140 in a plurality of axes such that adjustment in one axis is less likely to affect the adjustments in other axes.

In some implementations, the housing or cartridge generally remains in the same plane of orientation with respect to scanner 100 from the point that it is loaded into scanner 100 to the point at which it is ejected. This may apply to all operations of the scanner including the auto-focus and scan operations. For example, the cartridge may be received by the scanner at the load position in a vertical orientation, where probe array 140 would be located on one of the side faces of the cartridge. While remaining in the same vertical orientation the cartridge is placed into transport frame 205. Probe array 140, housed in the cartridge, is positioned into the best plane of focus by manipulating the cartridge via the pitch, roll, and Z mechanisms. The probe array is then scanned in the X axis by translation of lens 345 as well as the Y axis by translation of transport frame 205. After the completion of the scan operations the cartridge is returned to the load position via transport frame 205 in the same vertical orientation that it was received in.

Additional examples of cartridge transport frames and means for manipulating the position of a probe array for the purposes of scanning are described in U.S. patent application Ser. No. 10/389,194, incorporated by reference above.

Figure 4:
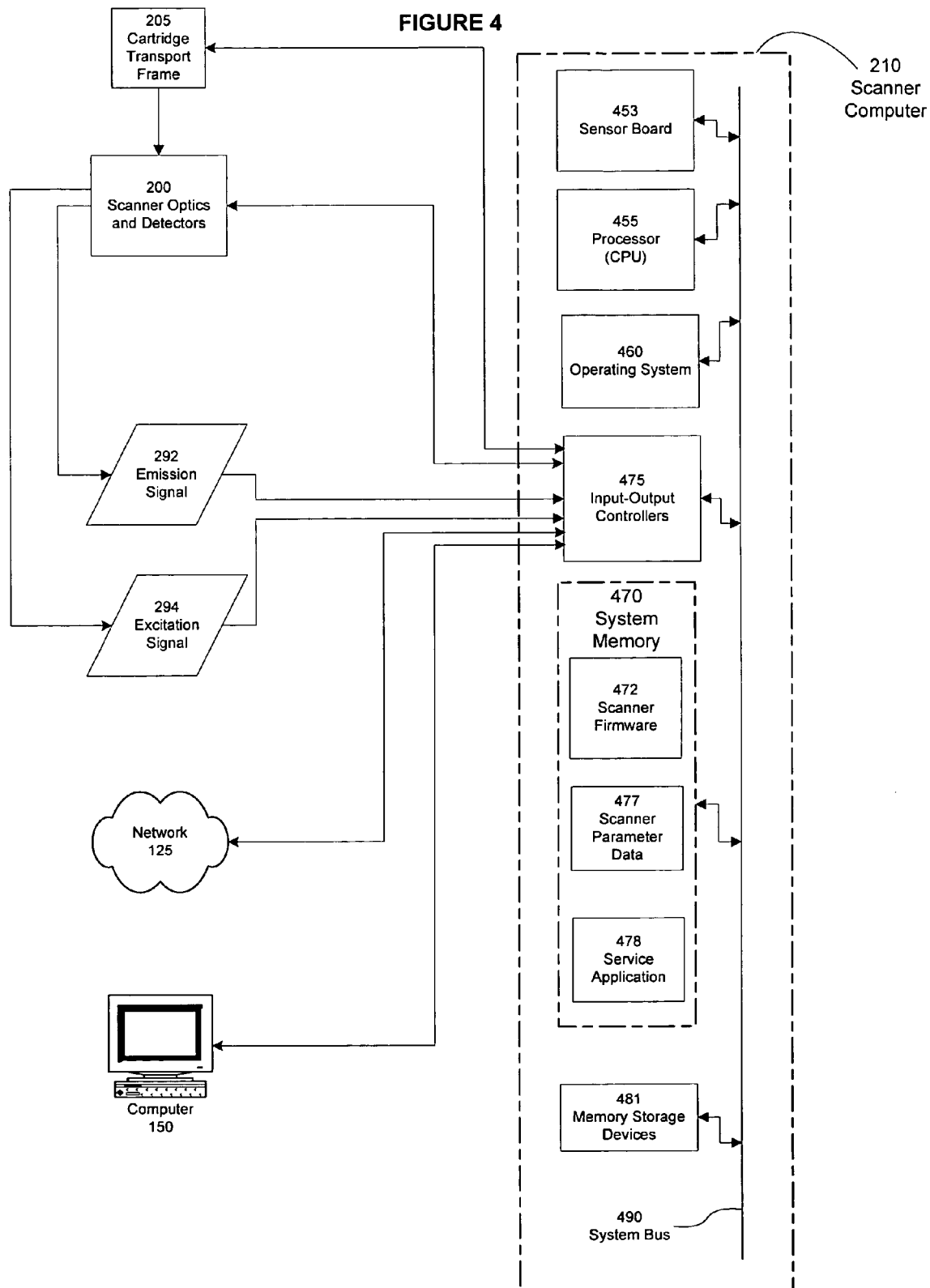
FIG. 4 is a functional block diagram of one embodiment of the scanner computer of FIG. 3, including a service application.

Scanner Computer 210: As illustrated in FIG. 4, scanner computer 210 may include elements such as sensor board 453, processor 455, operating system 460, input-output controllers 475, system memory 470, memory storage devices 481, and system bus 490 that may, in some implementations, have the same characteristics of corresponding elements in computer 150. Other elements of scanner computer 210 may include scanner firmware 472, and scanner parameter data 477 that will each be described in detail below.

Scanner firmware 472 may, in many implementations, be enabled to control all functions of scanner 100 based, at least in part, upon data stored locally in scanner parameter data 477 or remotely in one or more data files from one or more remote sources. For example, the remote data source could include computer 150 that includes library files 274, calibration data 276, and experiment data 277 stored in system memory 270. In the present example, the flow of data to scanner computer 210 may be managed by instrument control and image analysis applications 272 that may be responsive to data requests from firmware 472.

A possible advantage of including scanner computer 210 in a particular implementation is that scanner 100 may be network based and/or otherwise arranged so that a user computer, such as computer 150, is not required. Input-output controllers 475 may include what is commonly referred to by those of ordinary skill in the related art as a TCP/IP network connection. The term "TCP/IP" generally refers to a set of protocols that enable the connection of a number of different networks into a network of networks (i.e. the Internet). Scanner computer 210 may use the network connection to connect to one or more computers, such as computer 150, in place of a traditional configuration that includes a "hardwire" connection between a scanner instrument and a single computer. For example, the network connection of input-output controllers 475 may allow for scanner 100 and one more computers to be located remotely from one another. Additionally, a plurality of users, each with their own computer, may utilize scanner 100 independently. In some implementations it is desirable that only a single computer is allowed to connect to scanner 100 at a time. Alternatively, a single computer may interact with a plurality of scanners. In the present example, all calibration and instrument specific information may be stored in one or more locations in scanner computer 210 that may be made available to the one or more computers as they interface with scanner computer 210.

The network based implementation of scanner 100 described above may include methods that enable scanner 100 to operate unimpaired during averse situations that, for instance, may include network disconnects, heavy network loading, electrical interference with the network connection, or other types of adverse event. In some implementations, scanner 100 may require a periodic signal from computer 150 to indicate that the connection is intact. If scanner 100 does not receive that signal within an expected period of time, scanner 100 may operate on the assumption that the network connection has been lost and start storing data that would have been transmitted. When the network connection has been reacquired to scanner 100, all collected data and related information may be transferred to computer 150 that would have normally been transferred if the network connection remained intact. For example, during the occurrence of an adverse situation scanner 100 may lose the network connection to computer 150. The methods enable scanner 100 to operate normally including the acquisition of image data and other operations without interruption. Scanner 100 may store the acquired image data of at least one complete scanned image in memory storage devices 481 to insure that the data is not lost.

In some embodiments, scanner computer 210 may also enable scanner 100 to be configured as a standalone instrument that does not depend upon a controlling workstation. Scanner computer 210 may acquire and store image data as well as function as a data server to multiple clients for efficient data transfer. For example, memory storage devices 481 may include a hard disk or other type of mass storage medium that may be enabled to hold large volumes of image, calibration, and scanner parameter data. Scanner 100 may additionally include a barcode reader that reads one or more barcode identifiers from one or more barcode labels associated with probe array 140. Those of ordinary skill in the related art will appreciate that other means of identification may be used, such as Radio Frequency Identification (RFID), Magnetic strips, or other means known in the art, and that associated elements may be implemented in scanner 100 to enable their use. Scanner computer 210 may execute the scan operations based, at least in part, upon one or more data files associated with the identifiers, and store the acquired image data on the hard disk. Additionally, scanner 100 may provide a network file system or FIP service enabling one or more remote computers to query and upload scanned images as well as providing an interface enabling the computer to query scanner data and statistics.

It will be understood by those of ordinary skill in the related art that the operations of scanner computer 210 may be performed by a variety of other servers or computers, such as for instance computer 150, a server such as a GCOS server, or that computer 210 may not necessarily reside in scanner 100.

Figure 6A:
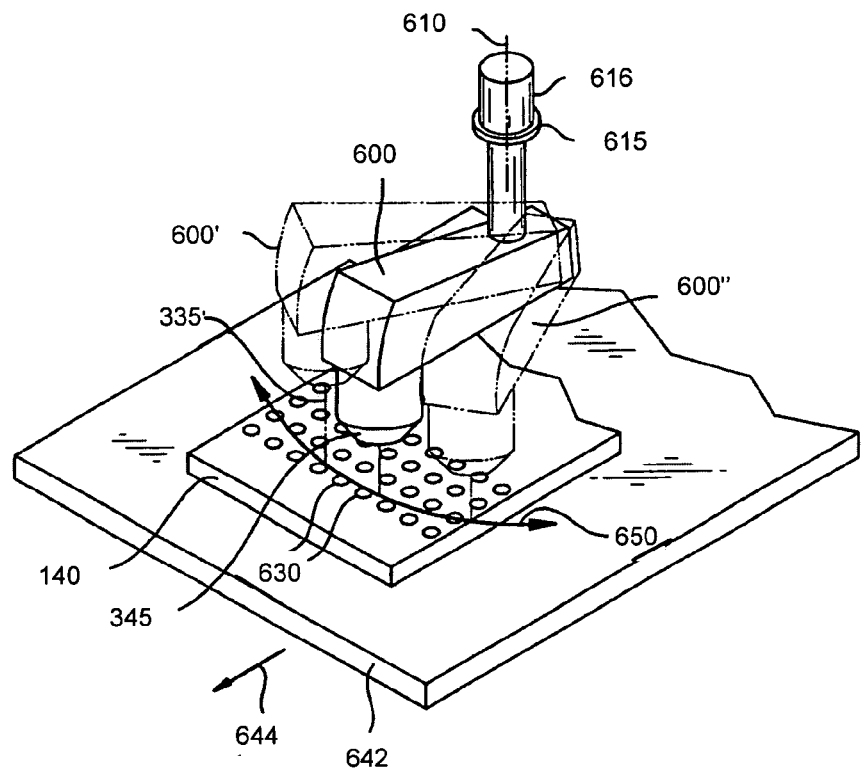
FIGS. 6A and 6B are graphical examples of one embodiment of a scanning arm suitable for translating an excitation beam over the probe array of FIG. 1.

Scanning Arm 600: FIG. 6A illustrates an example of a perspective view of a simplified representation of a scanning arm portion of scanner optics 200 in accordance with this particular, non-limiting, implementation. Scanning arm 600 moves in arcs around axis 610, which is perpendicular to the plane of galvo rotation. A position transducer may also be associated with arm 600. A possible benefit of this construction may be that the position of the oscillating arm itself is determined at each instant of data collection. Exact position data from the position transducer may be used for the construction of linearity correction tables and used for image correction methods. The position transducer, in accordance with any of a variety of known techniques, provides an electrical signal indicative of the radial position of arm 600. Certain non-limiting implementations of position transducers for galvanometer-driven scanners are described in U.S. Pat. No. 6,218,803 that is hereby incorporated by reference in its entirety for all purposes.

Figure 6B:
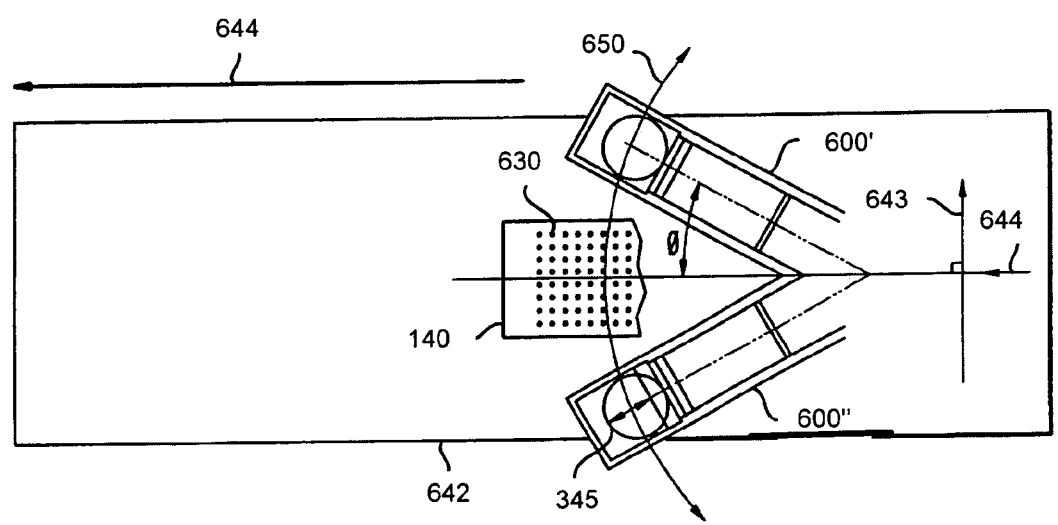

Arm 600 is shown in alternative position 600' and 600" as it moves back and forth in scanning arcs about axis 610. Excitation beam(s) 335' pass through objective lens 345 on the end of arm 600 and excites one or more labels such as fluorescent labels that may be associated with hybridized probe-target pairs in features 630 on a substrate of probe array 140, as further described below. The arcuate path of excitation beams 335' over probe array 140 is schematically shown for illustrative purposes as path 650. Emission beams 352 pass up through objective lens 345 as noted above. Probe array 140 of this example may be disposed on translation stage 642 that is moved in direction 644 so that arcuate path 650 repeatedly crosses the plane of probe array 140. The example of stage 642 is presented for the purposes of illustration only, and will be understood that other embodiments exist such as, for instance, one or more elements of cartridge transport frame 205 as described above. As is evident, the resulting coverage of excitation beams 335' over the plane of probe array 140 in this implementation is therefore determined by the footprint of beam, the speed of movement in direction 644, and the speed that arm 600 completes each pass of path 650. FIG. 6B provides an example of a top planar view of arm 600 with objective lens 345 scanning features 630 on probe array 140 as translation stage 642 is moved under path 650. As shown in FIG. 6B, arcuate path 650 of this example is such that arm 600 has a radial displacement of θ in each direction from an axis parallel to direction 644. For convenience of reference below, a direction 643 perpendicular to direction 644 is also shown in FIG. 6B. For illustrative purposes, direction 643 may hereafter be referred to herein as the "x" direction, and direction 644 as the "y" direction.

In some embodiments, the scan arm moves through a constant arc regardless of the array being scanned. As a result, the lens traverses the same distance over the array, and accordingly, the same number of pixels, regardless of where over the array the lens is traveling or the fluorescent material that may be present in the array. In addition, the time it takes for the lens to complete one pass and return back to a starting position is the same, for example in one possible implementation ⅟₅₀th of a second, regardless of the array being scanned or the fluorescent materials that may be present. Alternatively, some implementations may include the scan arm moving in an arc that is dependant upon the size of probe array 140. For example, the width of the arc for a particular probe array may be stored in scanner parameter data 477 that may be used by scanner firmware 472 to define the size of the arc.

Further details of confocal, galvanometer-driven, arcuate, laser scanning instruments suitable for detecting fluorescent emissions are provided in PCT Application PCT/US99/06097 (published as WO99/47964) and in U.S. Pat. Nos. 6,185,030; 6,201,639; and 6,225,625, all of which have been incorporated by reference above.

Service Application 278: It may be desirable in many embodiments to periodically calibrate scanner 100 to compensate for variations in components that could affect the proper acquisition of image data. Such variations could include those caused by mechanical wear or changes to one or more mechanical or optical elements. Those of ordinary skill in the related art will appreciate that mechanical or optical elements may be affected by a variety of factors including temperature fluctuation, mechanical wear, component imperfections, slight changes caused by physical insult, or other of a variety of possible factors. For example, scanner 100 could be initially calibrated at the factory, then periodically during routine service in the field by an instrument service engineer or other type of trained technician. Additional examples of calibration tools, procedures, and methods are described U.S. patent application Ser. Nos. 10/769,575, titled "System and Method for Calibration and Focusing a Scanner Instrument Using Elements Associated with a Biological Probe Array", filed Jan. 29, 2004; 10/770,717, titled "System, Method and Product for Gain Calibration in Optical Scanning Systems", filed Feb. 3, 2004; 10/868,590, titled "System and Method for Scanner Instrument Calibration Using a Calibration Standard", filed Jun. 14, 2004; and 10/389,194, titled "System, Method and Product for Scanning of Biological Materials", filed Mar. 14, 2003, each of which are hereby incorporated by reference herein in their entireties for all purposes.

In the above example, service application 278 allows user 101 to perform a plurality of calibration tests and procedures to insure that scanner 100 is operating within the proper technical specifications without the need for trained technical staff. Various implementations of service application may include tests and procedures such as what are referred to as Arc radius, X-Linearity, and Y-Linearity.

In some embodiments, service application 278 may provide a means for applications 272 to correct the placement of each pixel in an acquired image of probe array 140 to compensate for various sources of error associated with elements of scanner 100 so that the position of the pixel intensity in the image is the same as the actual position on probe array 140 from which the intensity data was derived. For example, service application 278 may work in association with scanner firmware 472 to generate one or more error tables from one or more scans of calibration features disposed upon one or more calibration arrays 142. Each error table may be stored as calibration data 276 for use by applications 272 during image analysis. Each error table may, for instance, specify one or measures and directional components that a particular pixel be "moved" or a measure of how far out of correct registration in the image the pixel is such as, for instance, by whole or fractional pixel increments in the plus or minus direction in the X and/or Y axes.

In some embodiments, an X-axis and/or a Y-axis linearity calibration table may be created or updated using a plurality of calibration features being disposed on a substrate of calibration array 142 in a grating or ladder pattern. For example, the ladder pattern may be constructed of chrome elements of known characteristics that may resemble a series of vertical bars arranged in a horizontal pattern with each bar spaced an equal distance apart. In the present example, it may be desirable that the position of the leading edge and width of each of the bars is exactly known. Alternatively a similar configuration may be used for what is referred to as Y-axis linearity calibration that includes the grating or ladder pattern of bars oriented in a vertical pattern instead of or in addition to the horizontal pattern. Also, some embodiments may include calibration array 142 that provides a geometric pattern of calibration features that perfectly corresponds to the placement of a grid pattern such as, for instance, a checkerboard type pattern that includes the same proportions and positional relationships among calibration features as the biological probe features of probe array 140. Those of ordinary skill in the related art will appreciate that the term "linearity calibration" generally refers to methods for the correction of error in one or more linear axes.

Continuing the example described above, calibration array 142 may be scanned and an image of the ladder pattern acquired along with positional data such as for instance, from a position transducer associated with the X-axis translation that could include a galvanometer arm, rotating mirror, voice coil, or other means of X-axis translation known in the art. Service application 278 may then compare the image positions of each of the calibration features, position data, and the known positions of leading edge of the associated calibration features, and generate an error table that includes one or more image correction values for each pixel position of an acquired image. In the present example, each of the correction values represents a measure of difference between the position detected by scanner 100 and the actual position in probe array 140. Application 272 may correct the placement of each pixel in an acquired or raw image or initial placement of a pixel value associated with emission signal 292 from probe array 140 based, at least in part, upon the error table that may, for instance, specify that a particular pixel be "moved" by whole or fractional pixel increments in the plus or minus direction in the X and or Y axes.

Also in some embodiments, implementations of calibration array 142 or one or more positional reference features associated with probe array 140 may be employed to measure the X-axis 643 span of measurement that may include an X-axis 643 distance associated with arcuate path 650. Alternative embodiments may also include the distance of translation of excitation beam 335' in X-axis 643 axis by means of a rotating mirror, voice coil, or other means of X-axis translation known in the art. For example, scanner 100 may include arm 600 or other means for X-axis 643 translation of excitation beam 335' across probe array 140 that travels a specified distance repeatedly for each pass over probe array 140, where the specified distance is also associated with a particular fixed number of pixels in an image generated by applications 272. In other words each pass of excitation beam 335' over probe array 140 measures light intensity for a pre-defined number of pixels over an expected X-axis 643 distance. Differences between what the actual X-axis 643 distance traveled by excitation beam 335' versus what the specified or expected X-axis 643 distance traveled may result in an actual change in the size or dimension of each pixel in a resulting image as a function of the degree of difference because the specified distance and number of pixels may be assumed to remain unchanged. For example, a specified or expected X-axis distance 643 may comprise a pre-defined number of pixels of the same, expected dimension contiguously arranged along X-axis 643. In the present example, when the X-axis distance increases or decreases from the specified or expected distance and the pre-defined number of pixels is unchanged, the result is a change in the dimension of actual pixel size. This can be problematic because but one or more algorithms employed by applications 272 may use the assumption of the expected pixel dimension in one or more image processing applications, thus introducing error into the resulting image data associated with the difference between the actual and expected pixel size.

For example, the difference between the actual pixel dimension and the expected pixel dimension has an additive effect in an image of probe array 140, where the image may include a pre-defined number of pixels that, for instance, may be greater than ten thousand pixels along the X-axis 643 distance. In the present example, the degree of difference between the actual and expected pixel dimension may be multiplied by the pre-defined number of pixels (i.e. the summation of degree of difference for each pixel in the line of pixels) that may result in the mis-registration of image elements and features, where if the difference is great enough could result in erroneous grid alignment and mis-interpretation of intensity data associated with specific probe features. Service application 278 may develop and/or update a pixel drift value associated with the degree of difference between the expected and actual X-axis 643 translation distance that is then applied by applications 272 to the image and correct the pixel dimension.

A method of determining a pixel drift value associated with a change in X-axis 643 distance may include the use of positional references associated with probe array 140 whose locations with respect to probe array 140 are known. In some embodiments, one or more methods already implemented for other purposes using positional reference elements could be employed for calculation of the pixel drift value. For example, in one possible embodiment the methods and elements employed for automatic focusing operations may be used to measure the actual span of the path 650 that is indicative of the X-axis 643 distance. In the present example, service application 278 and/or scanner firmware 472 may employ a chrome border or one or more other types of feature(s) located either in or around the active area of probe array 140 as positional reference locations, such as for instance control probe features, or alternatively reflective elements arranged at regular intervals in the active area that could include chrome crosshair type elements such as are described in U.S. patent application Ser. No. 10/769,575, titled "System and Method for Calibration and Focusing a Scanner Instrument Using Elements Associated with a Biological Probe Array", filed Jan. 29, 2004, which is hereby incorporated by reference herein in its entirety for all purposes.

Figure 7:
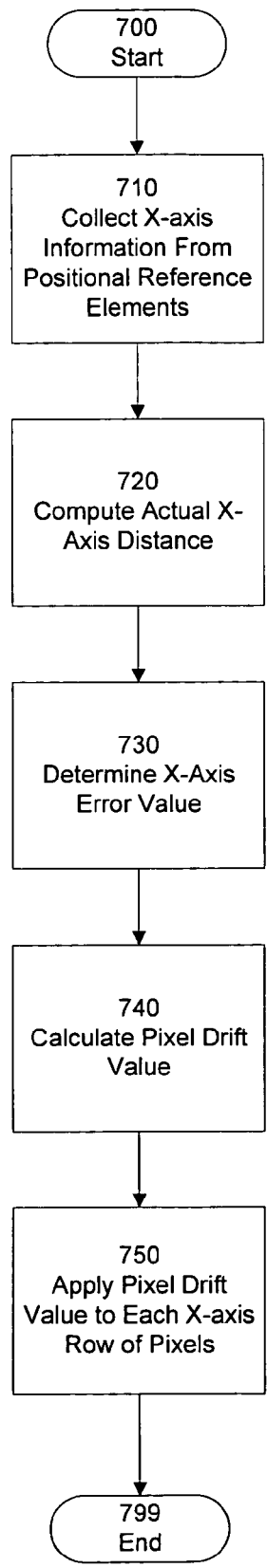
FIG. 7 is a functional block diagram of one embodiment of a method for calculating and applying a pixel drift value.

Illustrated in FIG. 7 is an example calculating and applying a pixel drift value after probe array 140 has been positioned in the plane of best focus. As illustrated in step 710, service application 278 and/or scanner firmware 472 may initiate the measurement of path 650 that is analogous to the X-axis 643 distance by performing at least one pass of excitation beam 335' along path 650, and in some implementations two or more passes including a pass at substantially both the top and bottom of probe array 140 collecting reflected or emitted light in response to beam 335' from the chrome border or other positional reference elements associated with probe array 140. The collected light associated with the chrome border or positional reference elements may then be employed by service application 278 and/or scanner firmware 472 to compute the actual X-axis 643 distance of span 650, as shown in step 720, by comparing the positional relationship of the known locations and detected image positions of the chrome border or positional reference elements for each pass of path 650. Step 730 illustrates the step of service application 278 and/or scanner firmware 472 subsequently comparing the actual X-axis 643 distance of path 650 to the assumed X-axis 643 distance of path 650 to determine an X-axis error value for path 650. In the embodiments where more than one pass has been employed the X-axis error values for each pass may be averaged or otherwise combined into a single error value. Step 740 illustrates the step of calculating a pixel drift value by dividing the X-axis error value by the pre-defined number of pixels. Next, step 750 illustrates the step of applying the pixel drift value to each X-axis row of pixels in a subsequently acquired image of the probe features of probe array 140. For instance, applications 272 may employ the pixel drift value to each pixel in an acquired image prior to grid placement in order to correct X-axis error generated by one or more elements of scanner 100 and result in proper registration of the grid to the image.

Figure 5:
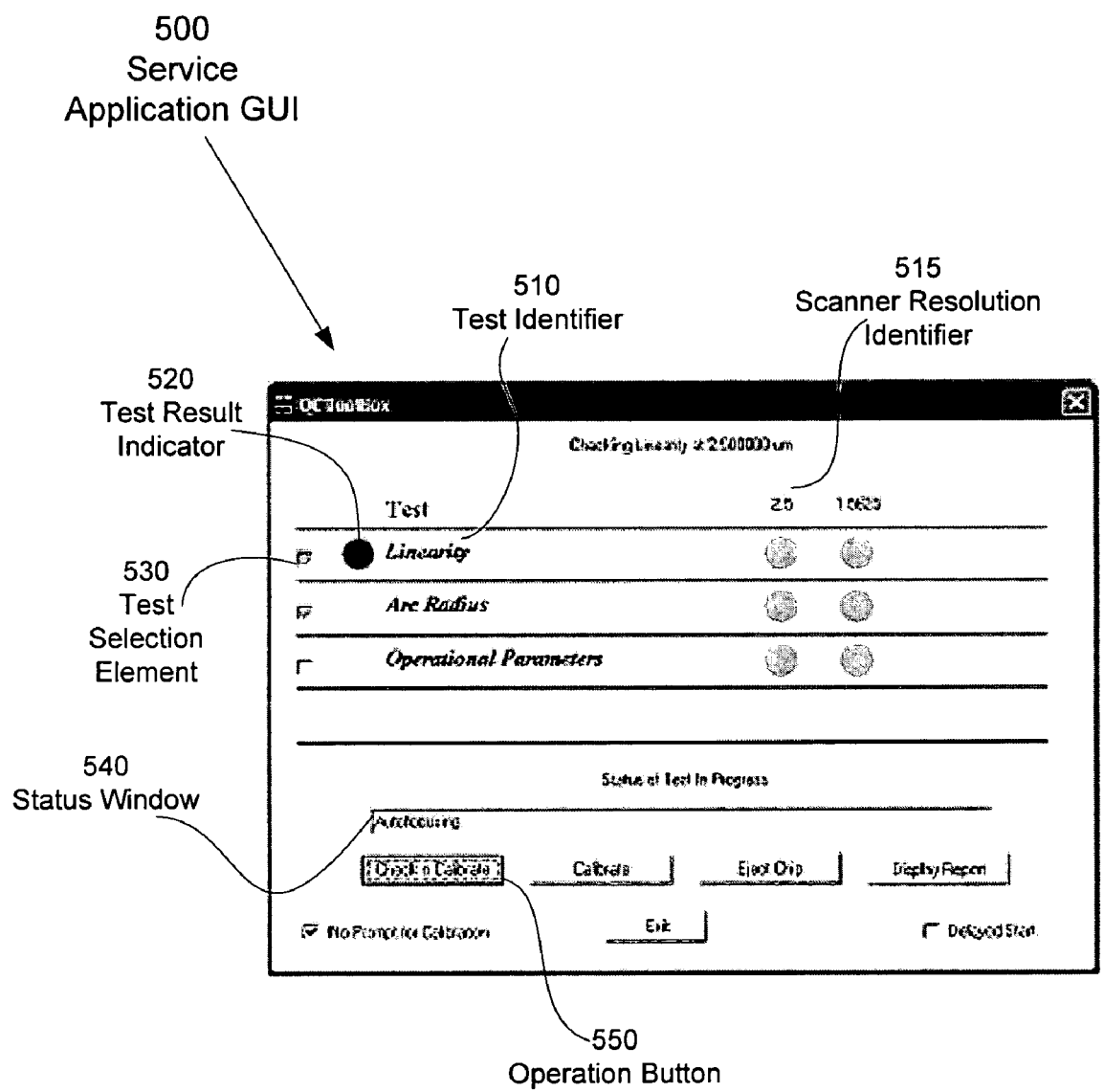
FIG. 5 is a graphical example of one embodiment of a graphical user interface provided by the service application of FIG. 4, enabled for user selection of one or more calibration functions.

Also, some embodiments of service application 278 may provide one or more means for a user selection of calibration tests and procedures, an example of which is provided in FIG. 5 as service application GUI 500. In the example provided by GUI 500, user 101 may select one or more calibration tests to be performed by selection of one or more test selection elements 530, positioned next to each associated test identified by test identifier 510. Service application 278 may indicate to user 101 the progress or status of each test in status window 540, and provide a visual indicator of test results and/or quality, indicated by test result indicator 520. For instance, indicator 520 could include a color code associated with result quality where green could be associated with a passing result, yellow with a marginal result, and red with a failing result. Service application 278 may also present one or more other windows or GUI's indicating test results.

Service application 278 may also display information associated with one or more characteristics of scanner 100, such as, for instance the pixel size or resolution of scanner 100 an example of which is presented as scanner resolution identifier 515 in FIG. 5.

GUI 500 may also present user 101 with a plurality of options for initiating operations. Displayed in FIG. 5 are operation buttons 550 that are user selectable for initiation of associated operations. For example, operations provided by buttons 550 may include checking the status of scanner 100 without changing the calibration, or alternatively calibrating scanner 100 without knowing whether or not scanner 100 was out of specification in one or more characteristics.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A method of determining a drift value, comprising:
performing one or more X-axis translations of an excitation beam over a probe array;
measuring light responsive to the excitation beam from at least two positional reference elements associated with the probe array for the X-axis translations;
calculating a distance value for the X-axis translation using a positional relationship of a known location associated with each of the positional reference elements and positions of the positional reference elements from the measured light; and
determining a drift value using a difference between the calculated distance value and an expected distance value.

2. The method of claim 1, further comprising:
applying the drift value to a plurality of pixels of an image of a plurality of probe features acquired from the probe array prior to grid placement.

3. The method of claim 2, wherein:
the drift value is applied to one or more pixels in a plurality of rows in the image.

4. The method of claim 1, wherein:
the X-axis translation of the excitation beam is performed by an element selected from the group consisting of a galvo arm, a rotating mirror, and a voice coil.

5. The method of claim 1, wherein:
the responsive light comprises reflected light.

6. The method of claim 1, wherein:
the responsive light comprises fluorescent light.

7. The method of claim 1, wherein:
the positional reference elements comprise at least two edges of a chrome border.

8. The method of claim 1, wherein:
the positional reference elements are located in the active area of the probe array.

9. The method of claim 8, wherein:
the positional reference elements comprise reflective elements.

10. The method of claim 8, wherein:
the positional reference elements comprise fluorescent control features.

11. The method of claim 1, wherein:
the drift value comprises a measure of error associated with each pixel in a row of pixels and is determined while acquiring sample image data.

12. The method of claim 11, wherein:
the row of pixels comprises a pre-defined number of pixels.

13. The method of claim 11, wherein:
the pixels are associated with an image of a plurality of probe features acquired from the probe array.

14. A system for determining a drift value, comprising:
a translation element that performs one or more X-axis translations of an excitation beam over a probe array;
one or more detectors that measure light responsive to the excitation beam from at least two positional reference elements associated with the probe array for the X-axis translations;
a software application stored for execution is system memory of a computer that performs the method of:
calculating a distance value associated with the X-axis translation;
determining a drift value using a difference between the calculated distance value and an expected distance value.

15. The system of claim 14, wherein:
the software application applies the drift value to a plurality of pixels of an image of a plurality of probe features acquired from the probe array prior to grid placement.

16. The system of claim 15, wherein:
the drift value is applied to one or more pixels in a plurality of rows in the image.

17. The system of claim 14, wherein:
the translation element is selected from the group consisting of a galvo arm, a rotating mirror, and a voice coil.

18. The system of claim 14, wherein:
the responsive light comprises reflected light.

19. The system of claim 14, wherein:
the responsive light comprises fluorescent light.

20. The system of claim 14, wherein:
the positional reference elements comprise at least two edges of a chrome border.

21. The system of claim 14, wherein:
the positional reference elements are located in the active area of the probe array.

22. The system of claim 21, wherein:
the positional reference elements comprise reflective elements.

23. The method of claim 21, wherein:
the positional reference elements comprise fluorescent control features.

24. The system of claim 14, wherein:
the drift value comprises a measure of error associated with each pixel in a row of pixels and is determined while acquiring sample image data.

25. The system of claim 24, wherein:
the measure of error is associated with one or more factors affecting the performance of the translation element.

26. The system of claim 25, wherein:
the one or more factors are selected from the group consisting of temperature fluctuation, mechanical wear, component imperfections, and physical insult.

27. The system of claim 25, wherein:
the row of pixels comprises a pre-defined number of pixels.

28. The system of claim 24, wherein:
the pixels are associated with an image of a plurality of probe features acquired from the probe array.

29. A method of correcting X-axis error in a probe array image, comprising:
performing one or more X-axis translations of an excitation beam over a probe array;
measuring light responsive to the excitation beam from at least two positional reference elements associated with the probe array for the X-axis translations;
calculating a distance value for the X-axis translation using a positional relationship of a known location associated with each of the positional reference elements and positions of the positional reference elements from the measured light;
determining a drift value using a difference between the calculated distance value and an expected distance value; and
applying the drift value to a plurality of pixels of an image of a plurality of probe features acquired from the probe array prior to grid placement.

30. A probe array scanner for correcting X-axis error in a probe array image, comprising:
a probe array scanner that comprises;
a translation element that performs one or more X-axis translations of an excitation beam over a probe array;
one or more detectors that measure light responsive to the excitation beam from at least two positional reference elements associated with the probe array for the X-axis translations; and
a software application stored for execution in system memory of a computer that performs the method of:
calculating a distance value for the X-axis translation using a positional relationship of a known location associated with each of the positional reference elements and positions of the positional reference elements from the measured light; determining a drift value using a difference between the calculated distance value and an expected distance value; and applying the drift value to a plurality of pixels of image of a plurality of probe features acquired from the probe array prior to grid placement.

* * * * *